United States Patent [19]

Cobia

[11] Patent Number: Plant 5,892

[45] Date of Patent: Feb. 24, 1987

[54] CACTACEAE PLANT

[75] Inventor: Barnell L. Cobia, Winter Garden, Fla.

[73] Assignee: B. L. Cobia, Inc., Winter Garden, Fla.

[21] Appl. No.: 739,443

[22] Filed: May 30, 1985

[51] Int. Cl.[4] ..... A01H 5/00

[52] U.S. Cl. ..... Plt./88

[58] Field of Search ..... Plt./88

*Primary Examiner*—Robert E. Bagwill

*Attorney, Agent, or Firm*—Roger L. Martin

[57] ABSTRACT

A new and distinct plant variety of the Cactaceae family which is sterile and in comparison to the 'Christmas Magic' variety is principally distinguished by a growth habit which includes a greater natural tendency for branching without the need for pruning, a greater resistance to nutrient deficiencies, a greater resistance to stem breakage, a slightly lesser resistance to bud abscission, a habit of producing more blooms on specimens of comparable age at an earlier date in the blooming season and with a slightly longer bloom life, and a habit of producing blooms with a fuller bodied appearance and enhanced color.

3 Drawing Figures

The invention relates to a new and distinct plant variety of the Cactaceae family and which has been named the *Zygocactus truncatus* 'Christmas Magic II' by the inventor.

Certain plant varieties of the Cactaceae family are well known in the foliage plant market and among these are the varieties of the *truncatus* species of the Zygocactus genus and which are commonly referred to as "Christmas Cactus" for they tend to bloom in the months of November and December in the Northern Hemisphere and hence appear in the retail market area primarily during Thanksgiving and Christmas seasons.

Among the various *Zygocactus truncatus* varieties are the 'Lavender Doll', 'Kris Kringle', and 'Christmas Magic' varieties. The 'Lavender Doll' variety has a generally "purplish" colored bloom and its characteristics are set forth in U.S. Plant Pat. No. 3,690. The 'Kris Kringle' variety has a generally "reddish" colored bloom and its characteristics are generally set forth in U.S. Plant Pat. No. 3,688. The 'Christmas Magic' variety has a generally "reddish purple" or "purplish red" colored bloom and its characteristics are generally set forth in U.S. Plant Pat. No. 4,197.

Each of the three mentioned varieties is a fertile variety and the 'Christmas Magic' variety has vastly improved growth habits in several areas when compared to the 'Lavender Doll' and 'Kris Kringle' varieties and which are of commercial significance. For example, the 'Christmas Magic' variety in comparison to the other two varieties has a greater natural tendency to branch and produce a larger number of phylloclades without inducement by pruning during the growth period prior to initial blooming. The variety also has a substantially greater resistance to bud abscission than the 'Lavender Doll' and 'Kris Kringle' varieties while nevertheless retaining a similar resistance to nutrient deficiencies and fungus type diseases.

A general objective of the invention has been to develop a sterile variety of the Cactaceae family which preserves or improves upon most of the commercially important growth habits of the 'Christmas Magic' variety and which provides a fuller bodied bloom with enhanced coloration. Other objectives have been to develop a sterile variety which exhibits many of the characteristics attributable to the 'Christmas Magic' variety but which is capable of withstanding a greater amount of handling without stem breakage, has a still greater natural tendency for branching without the need for pruning, and exhibits a greater resistance to nutrient deficiencies.

The objectives of the invention have been fully realized by the development of the new plant variety hereinafter described in detail. The new plant variety was developed in a nursery located at Winter Garden,. Fla., as a hybrid secured by cross pollinating the flower of a plant specimen of a research variety that is a descendant of the 'Kris Kringle' variety with pollen from a plant specimen of a research variety that is a descendant of the 'Lavender Doll' variety. The seeds taken from the sterilized seed pod were cultivated at the mentioned nursery location and after prolonged observation of the seedlings, the hybridized plant of the new plant variety was selected and asexually reproduced by the inventor at the Winter Garden nursery by the propagation of stem cuttings taken from the original hybrid plant. The maternal and paternal plant varieties are both research varieties that have not appeared in the market area.

Through successive propagations, it has been ascertained that specimens of the new plant variety generally resemble the 'Christmas Magic' variety but are distinguishable from specimens of this variety and the parent varieties, as well as other related varieties known to the inventor, by a growth habit which is evident in plant specimens propagated and grown under nursery conditions utilized in the growing of tropical plants at Winter Garden, Fla., as combining the following principal characteristics:

1. A growth rate, tendency for the formation of compact specimens, tendency for branching when pruned, specimen size at comparable stages of maturity and posture at maturity that are about the same as those of the 'Christmas Magic' variety while, nevertheless, having a greater natural tendency for branching without the need for pruning when compared to the 'Christmas Magic' variety.

2. A resistance to known problem diseases of the related varieties which is about the same as that found in the 'Christmas Magic' variety while, nevertheless, having a greater resistance to nutrient deficiencies than the 'Christmas Magic' variety.

3. A resistance to stem breakage which exceeds that of the 'Christmas Magic' variety and which is attributed to specimens with stems with greater flexibility in comparison to those of the 'Christmas Magic' variety.

4. A tendency for multiple bud formations on the tips of the branches that is about the same as that of the 'Christmas Magic' variety while, nevertheless, having a slightly lesser resistance to bud abscission in comparison to the 'Christmas Magic' variety.

5. A habit of producing more blooms on specimens of comparable age, at an earlier date in the blooming season, and with a slightly longer bloom life in comparison to the habits of the 'Christmas Magic' variety.

6. A habit of producing blooms with a fuller bodied appearance that is attributed to a substantially larger number of tepals in the tube laminating series of tepals and tepals in the tube laminating and tube forming series of tepals which average slightly greater width dimensions in comparison to those of the 'Christmas Magic' variety.

7. A bloom with enhanced coloration that is attributed to a greater and more uniform coverage of the marginal and center field areas of the blades of the tube laminating and tube forming series of tepals with color dominated by purplish red and/or reddish purplish hues in comparison to those of the 'Christmas Magic' variety.

8. Sterility.

The accompanying drawings serve by color photography to illustrate the new plant variety and wherein one sheet photographically illustrates a 20 month old plant specimen that was propagated in March, pruned to 2 tiers above the propagated stem cutting in August of the year of propagation and thereafter in July of the following year again pruned to the 3rd tier above the propagated stem cutting. Another sheet photographically illustrates a phylloclade and typical bloom of the new plant variety while the third sheet photographically illustrates the bloom as generally seen along the axis of the perianth tube.

The following is a detailed description of the new plant variety with colors and hues, unless otherwise clearly indicated by the text through the absence of color notations being named in accord with the ISCC-NBS Method of Designating Colors, (U.S. Dept. of Commerce, National Bureau of Standards, Circular 553, issued Nov. 1, 1955) the named colors being interpreted from color notations derived by comparison with the color specimens in the "Neighboring Hues Edition" of the Munsell Book of Color, published by the Munsell Color Company, Inc., of Baltimore, Md. The description is further based on observations of well fertilized plants of less than 2 years of age from initial propagation and which were grown under 50–75% shaded glasshouse nursery conditions in the Winter Garden, Fla. area and wherein temperatures ranges from about 60° F. to about 85° F. during the winter months, from about 75° F. to about 95° F. during the summer months, and are ambient during the intervening periods.

DETAILED PLANT DESCRIPTION

I. Name: *Zygocactus truncatus* 'Christmas Magic II'.

II: Parentage:

A. *Maternal.*—ZH5915-T, an unnamed research variety which is a descendant of *Zygocactus truncatus* 'Kris Kringle' (U.S. Plant Pat. No. 3,688) and in comparison to the new plant variety is a slightly slower grower with more frequent branching and a less erect posture, and has phylloclades that tend to be generally smaller in size and a slightly larger bloom with tepals which exhibit more recurve and a color that is less intense and perceptibly "redder".

B. *Paternal.*—ZH7505-T, an unnamed research variety which is a descendant of *Zygocactus truncatus* 'Lavender Doll' (U.S. Plant Pat. No. 3,690) and in comparison to the new plant variety has a comparable growth rate with less frequent branching, phylloclades that tend to be generally narrower, a blooming habit which is less prolific and slightly later in time, and a bloom with narrower tepals that have less recurve and a color which is more "purplish."

III. Classification:

A. *Botanic* (*Britton and Rose, The Cactaceae,* Constable and Co., Ltd., London 1937, Vol. L$).—(1) Family: Cactaceae. (2) Tribe: Cereeae. (3) Sub-tribe: Epiphyllanae. (4) Genus: Zygocactus. (5) Species: *truncactus* (Haworth) Schumann.

B. *Commercial.*—Thanksgiving-Christmas blooming cactus.

IV. Form: Epiphylic and terrestrial, shade loving, succulent, leafless plant with jointed and branched stems.

V. Stems:

A. *General.*—Irregular with usually multichotomous branching of both upright and pendulous, adventitiously rootable, flattened phylloclades that have a prominent midrib and prominently toothed lateral wings.

B. *Phylloclades.*—(1) General: Elongated and flat with a transversely elongated, areole bearing, truncated apex, with inwardly tapering basal wing margins that merge with a usually broadly pointed basal juncture with the phylloclade therebelow, and with an axially located areole usually being associated with each tooth. (2) Midrib: (a) General — Extends longitudinally of phylloclade and continuously through joints and with a laterally tapering cortex at the wing insertions. Pith surrounding vascular bundles that branch and provide lateral extensions of the vascular system to the marginal teeth. (b) Texture — Smooth, waxy epidermis with wax in small embedded scales and becoming woody in basal stem areas with specimen aging. (c) Size (at maturity) — 1. Length: Usually between 33 and 54 mm. 2. Thickness: Usually between 2 and 10 mm. (d) Color (at maturity) — Usually moderate olive green (7.5 GY $\frac{3}{4}$) (7.5 GY 4/6) (7.5 GY 4/4) and/or dark yellowish green (10 GY $\frac{3}{4}$). (3) Wings: (a) General — Dentate and generally flattened from midrib cortex to tooth insertions and with slight thinning taper toward margins. (b) Margins — Toothed. (c) Texture — Succulent to leathery with smooth, waxy epidermis where the wax is arranged in small embedded scales of higher density than in midrib area, and becoming corking in the basal stem areas with specimen aging. (d) Size (at maturity) — 1. Thickness: About 1.5–3 mm. in the area intermediate the margin and midrib. 2. Width: Usually 12–17 mm. as measured from phylloclade axis to most offset lateral areole. 3. Color (at maturity) — Usually moderate olive green (7.5 GY 4/6)

(7.5 GY ¾) (7.5 GY 4/4) (5 GY 4/4) and/or dark yellowish green (10 GY ¾). (4) Teeth: (a) Shape — 1. General: Generally flattened and tapered along the margins and from the wing insertion to an apex having a hyaline, single cell, pointed spine with nonpredictable bending, and with a tendency, that may be minimized or eliminated by selection, toward degenerate tooth formations in the lower quadrants of some phylloclades of some specimens. 2. Adaxial margin: Usually straight to convex. 3. Abaxial margin: Usually straight to concave. (b) Orientation — Usually project distally of phylloclade and laterally of the phylloclade axis in an alternate arrangement. (c) Margins — Entire. (d) Texture — Succulent to leathery with smooth waxy epidermis having wax in small embedded scales of density comparable to wings, and becoming corky in basal stem areas with specimen aging. (e) Size (at maturity) — 1. Thickness: Usually 0.75–1.5 mm. In center area. 2. Areole to apex dimension (adaxial marginal side): Usually 6–9 mm. in the upper quadrants of the phylloclades. (f) Number — Usually 6–8 per phylloclade. (g) Color — Usually moderate olive green (7.5 GY ¾) (7.5 GY 4/4) (5 GY 4/4). (5) Areoles: (a) Terminal areole — Large, elongated, oval shaped with several acicular bristles, and several buds that may mature into either new phylloclades or flowers. The opposite ends of the areole are located adjacent to subsidiary areoles which are in turn located at the axils of the teeth at the distal end of the phylloclade. (b) Axillary areoles — Acicular bristles without glochidia but having copious, short, brownish, multicellular, wooly hairs. In areoles located below the teeth at the distal end of the phylloclade, there is usually only one areole which is frequently latent.

VI. Buds: Unarmored, ovoid and chlorophyllous.

VII. Flowers:

A. *General.*—Sessile, zygomorphic, usually solitary, terminal, perfect and epigynous with double hypanthium and whorled tepals (undifferentiated sepals and petals) having a spiral emergence as a perianth provided with a sepaloid series of free tepals, a tube laminating series of tepals, and a tube forming series of united tepals.

B. *Sepaloid series.*—(1) General: Free tepals inserted on top of ovary. (2) Shape: Deltoid in outer members of whorl and grading inwardly in the whorl to provide progressively greater length dimensions and broader apices. All members have a pointed tip and entire margins with sparse irregular teeth appearing mainly in the apex areas of the inner members of the whorl. (3) Texture: Succulent and glabrous outer whorl members and grading inwardly in whorl to silken blades with fleshy basal areas. (4) Number: Usually 4–5. (5) Size (at full bloom): (a) Length (base-tip dimension) — Usually less than 15 mm. (b) Blade with (maximum) — Usually less than 15 mm. (6) Color (at full bloom): Varies from the outer members to the inner members with the smallest outer whorl tepals usually having a continuous field that in color is dominated by a yellow green hue. The inner whorl tepal members have marginal blade and blade center field areas that in color are dominated by purplish red, purplish pink and/or pink hues that project into a translucent white basal area. Commonly moderate purplish red (7.5 RP ⅝) (10 RP 5/10), dark purplish red (5 RP 6/8) and/or deep pink (10 RP 6/10) in marginal and center field areas of the inner whorl members and moderate yellow green (2.5 GY 7/6) and/or strong yellow green (5 GY 7/8) in the basal areas of outer whorl members. (7) Orientation: Erect to recurve at full bloom.

C. *Tube laminating series.*—(1) General: Tepals inserted on ovary and basally united below the throat as outer laminations on the perianth tube and with progressively greater amount of basal fusion inwardly in the whorl. (2) Shape: Zygomorphic and grading inwardly in the whorl with progressively greater length dimensions and broader apices so that the blade area changes inwardly in the whorl from ovate with an acute tip to spatulate with a broader acute tip. Entire margins with sparse, irregular teeth mainly in apex areas. (3) Texture: Succulent and glabrous outer whorl members and grading inwardly to silken blades with slightly fleshy basal areas. (4) Number: Usually 6–9 tepals. (5) Size (at full bloom): (a) Length (base-tip dimension) — Usually between 19 and 48 mm. (b) Width (maximum) — Usually between 12 and 21 mm. (6) Color (at full bloom): (a) General — Tepals with basal areas that are dominated by a purplish pink hue immediately above insertion and marginal blade and blade center field areas that in color are dominated by a purplish red hue which merges with the distally extending basal area colors. (b) Basal area — Translucent white at insertion and usually pale purplish pink (7.5 RP 8/2) along tube attached area. (c) Blade area — Usually moderate purplish red (5 RP ⅝) and/or grayish purplish red (5 RP 5/6) in marginal and center field areas. (7) Orientation: Perpendicular to recurve at full bloom.

D. *Tube forming series.*—(1) General: Tepals basally united to form hollow perianth tube that is inserted on ovary and equipped at its throat with an irregular carina (keel). (2) Shape: (a) Perianth tube — Elongated and ellipsoidal in cross section with the major ellipsoidal axis usually generally normal to the plate of the supporting phylloclade. (b) Blades — Nearly zygomorphic and thinly spatulate with acute tips and entire margins having sparse irregular teeth in apex area. (c) Carine (keel) — Degenerate and reduced to a slight superior extension of the perianth tube. (3) Texture: (a) Perianth tube — Thick, succulent and slightly ribbed. (b) Blades — Translucent and silken. (c) Carina (keel) — Fleshy. (4) Number: Usually 6–9. (5) Size (at full bloom): (a) Perianth tube — 1. Length (base-keel): Usually 30–33 mm. along tube axis. 2. Major Axis: Usually 8–11 mm. at throat interior. 3. Minor axis: Usually 7–9 mm. at throat interior. (b) Blades — 1. Length (keel-tip): Usually 28–39 mm. 2. Width (maximum): Usually 13–20 mm. (6) Color (at full bloom): (a) Perianth tube — A basic field that is translucent white with longitudinally extending, randomly arranged striations or streaks that in color are dominated by a purplish pink hue.

Commonly deep purplish pink (5 RP 6/10). (b) Blades — Marginal and center field areas that are nearly uniform in color at and distally of the keel and dominated by reddish purple and/or purplish red hues. Commonly strong reddish purple (5RP 5/10) (2.5 RP 4/10) (2.5 RP 5/12), vivid reddish purple (2.5 RP 5/14) (2.5 RP 4/14), strong purplish red (5 RP 5/12) and/or vivid purplish red (5 RP 5/14). (c) Carina (keel) — Color dominated by reddish purple and/or purplish red hues and constituting a continuation of the blade color. Commonly strong reddish purple (5 RP 5/10) (2.5 RP 4/10) (2.5 RP 5/12), vivid reddish purple (2.5 RP 5/14) (2.5 RP 4/14), strong purplish red (5 RP 5/12) and/or vivid purplish red (5 RP 5/14). (7) Orientation: Acute to recurve.

E. *Androecium* (*stamens*).—(1) General: Numerous exserted and diadelphous stamens with one group having filaments basally fused to the perianth tube and the other group having filaments basally united to form a nectary housing, thin annulus around the style and which is provided with thin, deflexed, irregular, toothed margin or ruffle at the throat of the annulus. (2) Stamen number: (a) Tube attached group — Usually 58–65. (b) Basally united group — Usually 17–19. (3) Filaments: (a) General — Translucent white with anther (connective. (b) Shape — Long, slender, terete. (c) Texture — Glabrous and capillaceous. (d) Color — Color dominated by a pink hue in the distal area and which merges at a distance of about ⅓ of the length from the distal end of the filament with a translucent white color that dominates in the basal area. Commonly light pink (near 10 RP 8/4) and/or moderate pink (near 10 RP 8/4) in the distal area. (e) Size (at full bloom — 1. Length: (a) Tube attached group — Usually between 45–55 mm. (b) Basally united group — Usually between 40–45 mm. 2. Diameter: Usually about 0.5 mm. at insertion and tapering to about 0.25 mm. at distal end. (4) Anthers (a) General — Adnate with four longitudinally dehiscent pollen sacs and connective inserted at end. (b) Shape — Elongated. (c) Texture — Waxy. (d) Color (before dehiscence) — Dominated by a purplish pink hue. Commonly moderate purplish pink (5 RP 7/6) and/or light purplish pink (5 RP 8/6). (e) Sterility — Sterile.

F. *Gynoecium* (*pistil*).—(1) General: Exserted with compound, parietal placentation and united style surrounded by annular diffuse yellowish nectary at its insertion. (2) Style: (a) General — Stout and inserted at ovary. (b) Shape — Elongated and terete. (c) Texture — Fleshy and smooth. (d) Color — Dominated by a purplish pink hue at the basal end and progressively varying to a color dominated by a purplish red hue at the distal end. Commonly moderate purplish pink (5 RP 7/8) at basal end and moderate purplish red (5 RP 5/10) at distal end. (e) Size (at full bloom — 1. Length: Usually 60–65 mm. 2. Diameter: Usually 1–1.5 mm. intermediate opposite ends. (3) Stigma: (a) General — Exserted and erect with usually 5–7 inner marginally adhering lobes. (b) Shape — Elongated and tapering toward lobe tips and having relatively blunt apices. (c) Texture — Fleshy and smooth with inner sides of lobes having short glutinous capillaceous hairs. (d) Color — Dominated by purplish red and/or purplish pink hues. Commonly moderate purplish red (5 RP 5/10), dark purplish pink (5 RP 6/8) and/or deep purplish pink (5 RP 6/10). (e) Size — 1. Length: Usually 3–4 mm. along inner margins of lobes. (4) Ovary: (a) General — Inferior with thin epidermis and usually 5–6 carpules with numerous ovules. (b) Shape — Terete to ovoid and generally broadening from insertion to floral end. Ribbed single concavity with inserted style. (c) Texture — Succulent with glabrous thin outer epidermis. (d) Color — Usually moderate olive green (2.5 GY 5/6) (2.5 GY 6/4) (2.5 GY 6/6). (e) Size — 1. Length: Usually 6–11 mm. from insertion to cavity base. 2. Major axis: Usually 8–11 mm. at distal end of concavity. 3. Minor axis: Usually 2–3 mm. at distal end of concavity.

VIII. Growth habit: The new plant variety has an upright and compact (dense) appearance, and a fast growth rate comparable to the 'Christmas Magic' variety but nevertheless productive of more phylloclades than the 'Christmas Magic' variety without inducement by pruning during the growth period preceding blooming. The new variety also has a resistance to stem breakage which exceeds that of the 'Christmas Magic' variety.

Apart from the greater natural tendencies for branching without pruning, the tendencies for branching when pruned are about the same as those of the 'Christmas Magic' variety. The new variety has about the same resistance as the 'Christmas Magic' variety to known problem diseases of the related varieties but nevertheless has a greater resistance to nutrient deficiencies than those shown by the 'Christmas Magic' variety. The new variety exhibits a similar tendency for multiple bud formations on the tips of the branches as shown by the 'Christmas Magic' variety but in comparison exhibits a slightly lesser resistance to bud abscission.

In comparison to the 'Christmas Magic' variety, the new variety has a habit of producing more blooms on specimens of comparable age, at a slightly earlier date in the blooming season, and the blooms exhibit a slightly longer bloom life, ranging from about 7 to 10 days. The blooms produced on specimens of the new variety have a fuller bodied appearance that is attributed to a larger number of tepals in the tube laminating series of tepals and to tepals in the tube laminating and tube forming series which average slightly greater width dimensions in comparison to those of the 'Christmas Magic' variety. The bloom also exhibits enhanced coloration in comparison to the 'Christmas Magic' variety and this is attributed to a greater and more uniform coverage of the marginal and center field areas of the blades of the tube laminating and tube forming series of tepals with color which is dominated by purplish red and/or reddish purple hues.

The following is a general description of a specimen of the new plant variety which was grown from the propagation of a single phylloclade in a nursery at Winter Garden, Fla.

Age of plant: 20 months from initial propagation of single phylloclade. The specimen was pruned to the second tier above the propagated phylloclade during the sixth month and thereafter to the third tier above the propagated phylloclade during the seventeenth month following propagation.

Branches from propagated phylloclades: 2.

Total number of new phylloclades on specimen: 77.

General:

| Branch No. | No. of Phylloclades | Max. Length | No. of Tips |
|---|---|---|---|
| 1 | 40 | 53 | 15 |
| 2 | 37 | 50 | 14 |

Midribs:

| Branch No. | Length (avg.) | Thickness (avg.) |
|---|---|---|
| 1 | 42.2 mm. | 3.42 mm. |
| 2 | 41.0 mm. | 3.54 mm. |

Wings:

| Branch No. | Center Thickness (avg.) | Max. Width (avg.) |
|---|---|---|
| 1 | 1.6 mm. | 12.47 mm. |
| 2 | 1.7 mm. | 11.29 mm. |

Teeth:

| Branch No. | No. per Phylloclade (avg.) | Center Thickness (avg.) | Areole to Apex Length (avg.) |
|---|---|---|---|
| 1 | 6.7 | 1.31 mm. | 6.06 mm. |
| 2 | 7.2 | 1.26 mm. | 5.53 mm. |

Phylloclade color: Moderate olive green to dark yellowish green.

The following is a general description of a flower of the new plant variety and which bloomed in December on the 20 month old plant specimen mentioned above, the plant specimen having been grown under shaded greenhouse nursery conditions in Winter Garden, Fla.

No. of buds and blooms on plant specimen: 26.

Bloom life: 8 days.

Sepaloid series of tepals:

*Number.*—5.

*Size (at full bloom).*—Maximum base-tip dimension: 15 mm. Minimum base-tip dimension: 2 mm. Maximum width dimension: 15 mm.

*Color (at full bloom).*—Dark purplish pink and/or moderate purplish red in continuous field of outer whorl members of small tepals. Dark purplish pink and/or moderate purplish red in marginal and center field areas and strong yellow green to moderate yellow green in the basal areas of the inner whorl members.

Tube laminating series of tepals:

*Number.*—8.

*Size (at full bloom).*—Maximum base-tip dimension: 47 mm. Minimum base-tip dimension: 20 mm. Maximum blade width: 20 mm. Minimum blade width: 15 mm.

*Color.*—Moderate purplish red and/or grayish purplish red in marginal and center field areas of the blades and pale purplish pink in the basal areas of the blades.

Tube forming series of tepals:

*Number.*—8.

*Size (at full bloom).*—Perianth tube: Length (base to keel) — 32 mm. along tube axis. Major axis — 13 mm. at throat interior. Minor axis — 7 mm. at throat interior. Blades: Maximum length (keel-tip) — 32 mm. Minimum length (keel-tip) — 29 mm. Maximum blade width — 17 mm. Minimum blade width — 15 mm.

*Color.*—Perianth tube: A major field of white with random striations of deep purplish pink. Blades: Strong reddish purple in basal areas of blades and strong purplish red in marginal and center field areas of the blades.

Androecium:

*Stamen number.*—Tube attached group: 63. Basally united group: 18.

*Filaments.*—Color: White to pinkish white in basal area and light pink in distal area. Size (at full bloom): Length — Tube attached group: 50 mm. (avg.). Basally united group: 42 mm. (avg.). Diameter: About 0.35 mm. intermediate the opposite ends.

*Anthers.*—Color (before dehiscing): Moderate purplish pink and/or light purplish.

Gynoecium (pistil):

*Style.*—Color: Moderate purplish pink in basal area and moderate purplish red in distal area. Size (at full bloom): Length — 63 mm. Diameter — 1.2 mm. intermediate the opposite ends.

*Stigma.*—Color: Moderate purplish red, dark purplish red, and/or deep purplish pink. Size: 3.5 mm. (avg.) lobe length.

*Ovary.*—Color: Moderate yellow green. Size (at full bloom): Major axis — 10 mm. at distal end of concavity. Minor axis — 2.5 mm. at distal end of concavity.

I claim:

1. The new and distinct plant variety of the Cactaceae family as described and illustrated herein and which is principally distinguished by a growth habit combining the following characteristics:

(1) a greater natural tendency for branching without the need for pruning than the 'Christmas Magic' variety, (2) a greater resistance to nutrient deficiencies than the 'Christmas Magic' variety, (3) a greater resistance to stem breakage than the 'Christmas Magic' variety, (4) a slightly lesser resistance to bud abscission than the 'Christmas Magic' variety, (5) a habit of producing more blooms on specimens of comparable age at an earlier date in the blooming season, and with a slightly longer bloom life than the 'Christmas Magic' variety, (6) a habit of producing blooms with a substantially larger number of tepals in the tube laminating series of tepals, and with tepals in the tube laminating and tube forming series of tepals which average slightly greater width dimensions in comparison to the 'Christmas Magic' variety, (7) a bloom with more uniform and greater coverage of the marginal and center field areas of the blades of the tube forming and tube laminating series of tepals with color dominated by purplish red and/or reddish purplish hues in comparison to the 'Christmas Magic' variety, (8) sterile specimens.

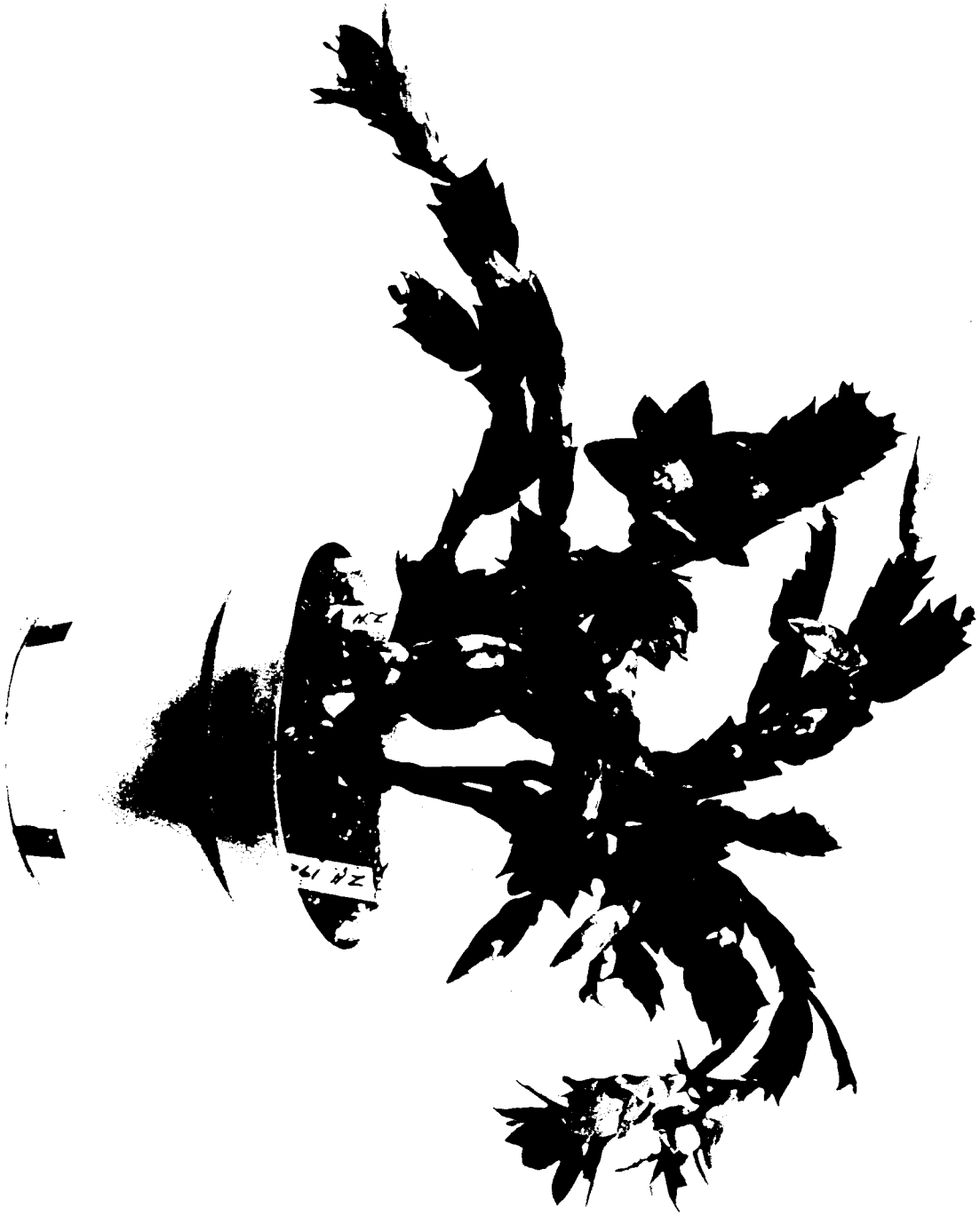

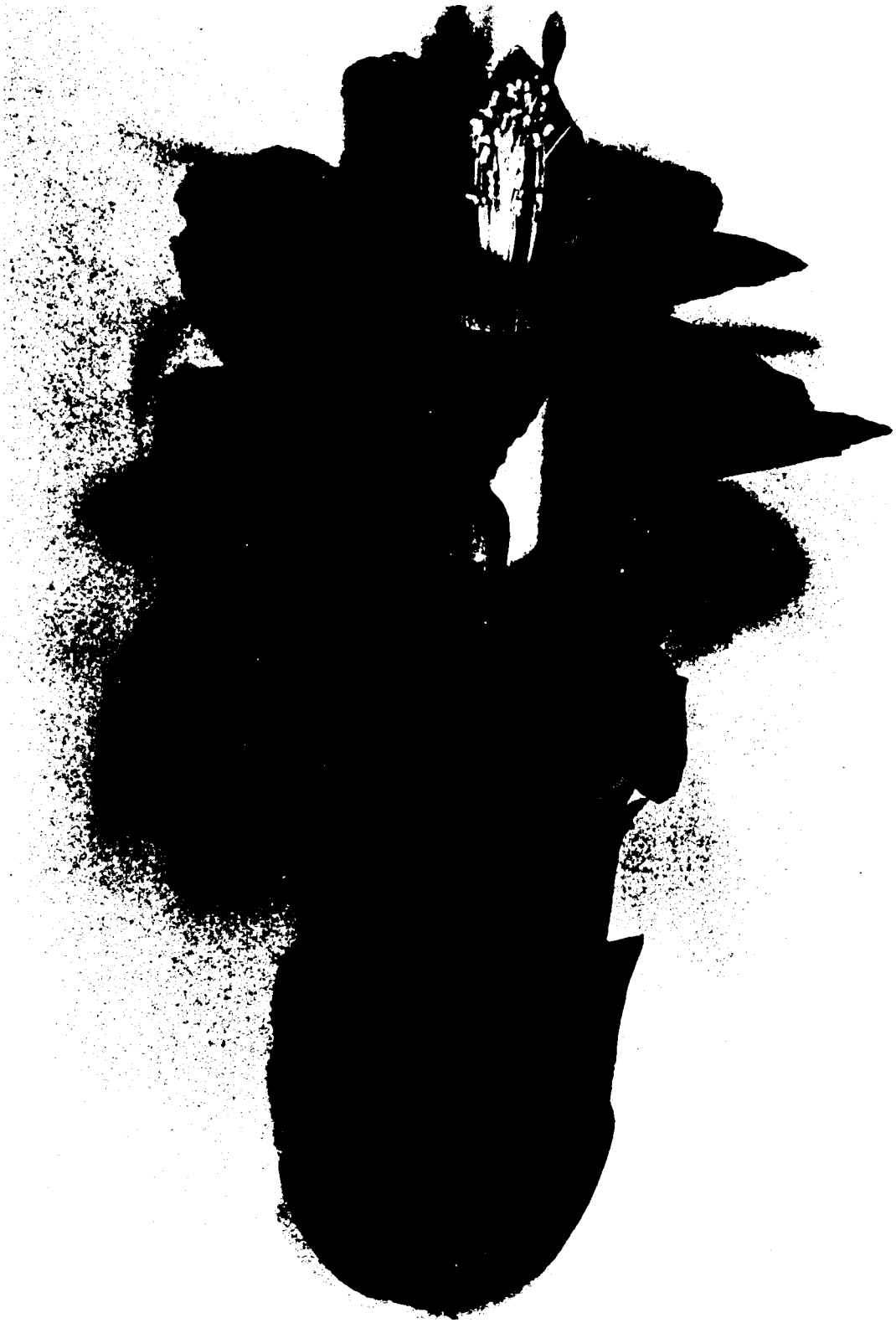

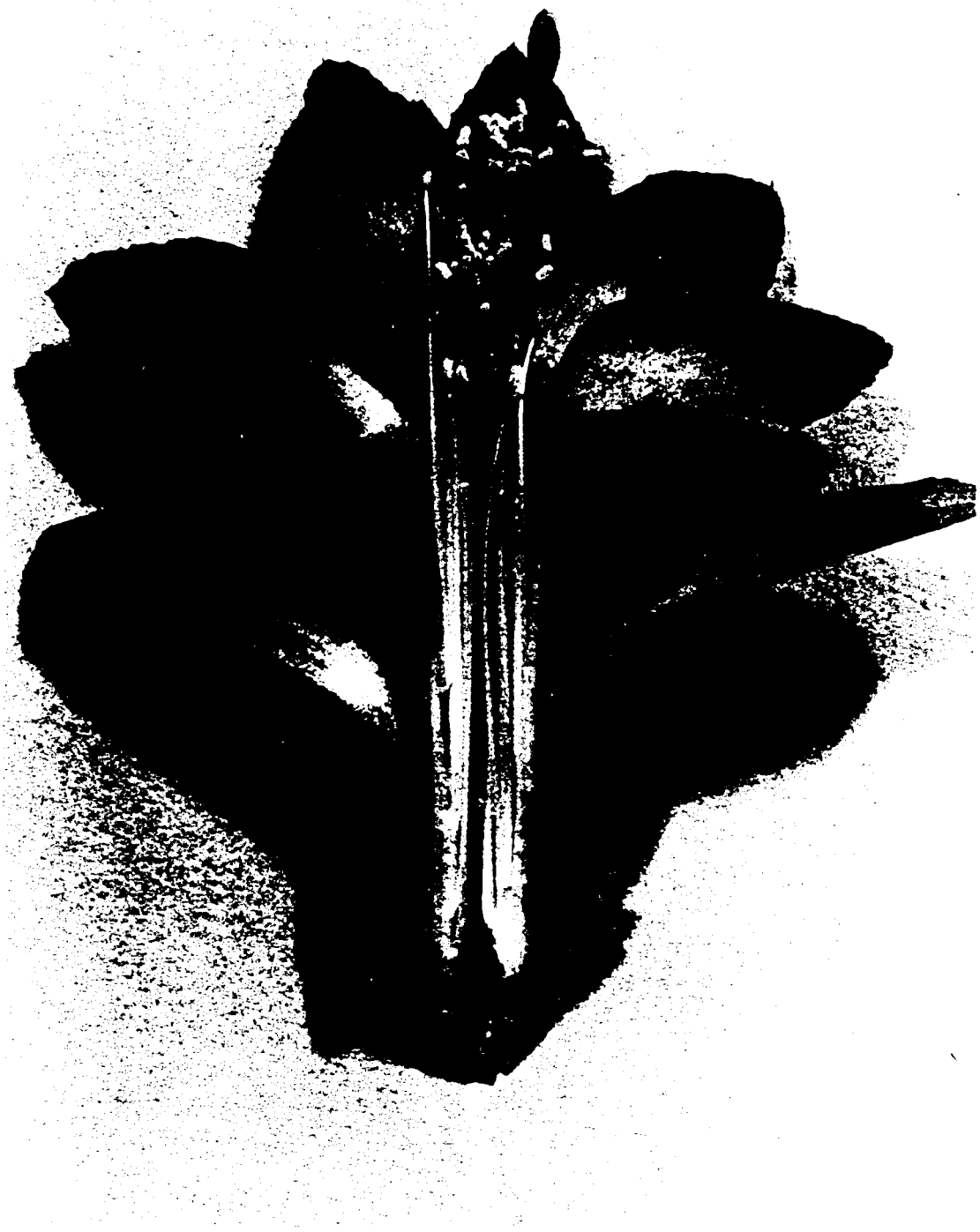

* * * * *